(12) United States Patent
Kowarsch et al.

(10) Patent No.: US 8,784,423 B2
(45) Date of Patent: Jul. 22, 2014

(54) TIBIAL CROSS-PIN FIXATION TECHNIQUES AND INSTRUMENTATION

(75) Inventors: Markus Kowarsch, Munich (DE); Dominik Steffens, Munich (DE); Gerlinde Michel, Munich (DE); Hans Linden, Cologne (DE); Nick J. T. Metcalfe, Munich (DE); Jacob A. Jolly, Naples, FL (US)

(73) Assignee: Arthrex, Inc., Naples, FL (US)

( * ) Notice: Subject to any disclaimer, the term of this patent is extended or adjusted under 35 U.S.C. 154(b) by 431 days.

(21) Appl. No.: 13/109,390

(22) Filed: May 17, 2011

(65) Prior Publication Data
US 2011/0282350 A1 Nov. 17, 2011

Related U.S. Application Data

(60) Provisional application No. 61/345,491, filed on May 17, 2010.

(51) Int. Cl.
*A61B 17/56* (2006.01)
*A61B 17/17* (2006.01)

(52) U.S. Cl.
USPC .......................................... 606/86 R; 606/96

(58) Field of Classification Search
USPC ................................ 606/86 R, 87–88, 96–98
See application file for complete search history.

(56) References Cited

U.S. PATENT DOCUMENTS

| | | | | |
|---|---|---|---|---|
| 5,918,604 A | * | 7/1999 | Whelan | 128/898 |
| 6,187,011 B1 | * | 2/2001 | Torrie | 606/96 |
| 7,500,990 B2 | * | 3/2009 | Whelan | 623/13.14 |
| 7,637,910 B2 | * | 12/2009 | Schmieding et al. | 606/80 |
| 7,914,545 B2 | * | 3/2011 | Ek | 606/180 |
| 2004/0199166 A1 | | 10/2004 | Schmieding et al. | |
| 2007/0233151 A1 | * | 10/2007 | Chudik | 606/96 |
| 2008/0039852 A1 | * | 2/2008 | Schmieding et al. | 606/88 |
| 2008/0046009 A1 | * | 2/2008 | Albertorio et al. | 606/232 |
| 2009/0275950 A1 | | 11/2009 | Sterrett et al. | |

* cited by examiner

*Primary Examiner* — Nicholas Woodall
*Assistant Examiner* — Larry E Waggle, Jr.
(74) *Attorney, Agent, or Firm* — Dickstein Shapiro LLP

(57) ABSTRACT

Techniques and reconstruction systems for ACL repair by providing cross-pin fixation of a graft within a tibial tunnel. The invention provides tibial fixation techniques according to which cross-pin fixation of a graft (for example, an Anterior Tibialis allograft) is achieved on the tibial side, close to the jointline, by a single incision and with cortical fixation.

20 Claims, 18 Drawing Sheets

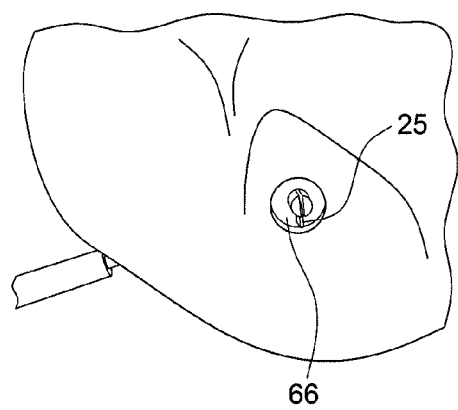
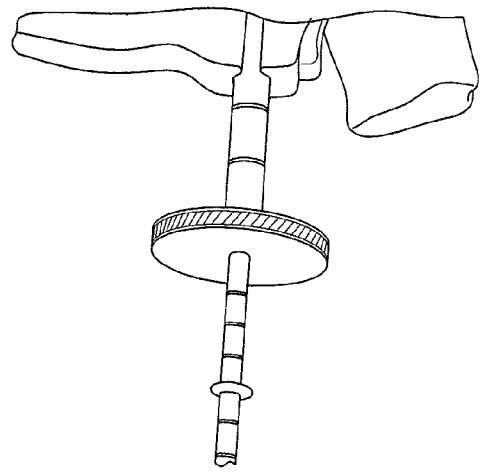
FIG. 9        FIG. 10
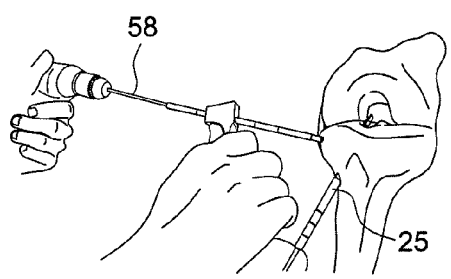
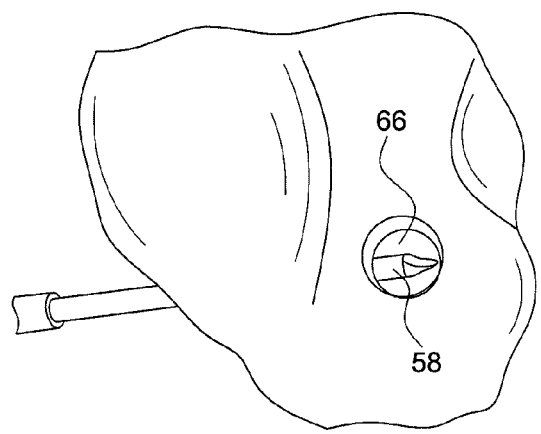
FIG. 11       FIG. 12

TIBIAL CROSS-PIN FIXATION TECHNIQUES AND INSTRUMENTATION

CROSS-REFERENCE TO RELATED APPLICATIONS

This application claims the benefit of U.S. Provisional Application No. 61/345,491, filed May 17, 2010, the entire disclosure of which is incorporated by reference herein.

FIELD OF THE INVENTION

Embodiments of the invention relate to the field of surgery and, more particularly, to methods and apparatus for improved graft fixation in ACL reconstructive surgeries.

BACKGROUND OF THE INVENTION

Reconstructive surgeries, particularly anterior cruciate ligament (ACL) reconstruction, are well-known in the art. In general, these methods of tenodesis involve drilling a tunnel through the tibia, drilling a closed tunnel (socket) into the femur, inserting a substitute ACL graft into the tunnels, and securing the graft to the walls of the tibial and femoral tunnels using interference screws or the like. Cross-pin ACL fixation is also known, as described for example in U.S. Pat. No. 5,918,604, in which the graft is looped over a pin inserted transversely across the femur, intersecting a socket formed in the femur, in a system known as TransFix fixation. To date, however, cross-pin ACL fixation has been limited to fixation of the graft in the femur.

BRIEF SUMMARY OF THE INVENTION

The present invention provides techniques and reconstruction systems for ACL repair by providing cross-pin fixation of the graft within the tibial tunnel. The invention provides tibial fixation techniques according to which cross-pin fixation of a graft (for example, an Anterior Tibialis allograft) is achieved on the tibial side, close to the jointline, by a single incision and with cortical fixation.

Other features and advantages of the present invention will become apparent from the following description of the invention which refers to the accompanying drawings.

BRIEF DESCRIPTION OF THE DRAWINGS

FIGS. 1-28 illustrate various steps of a method of ACL reconstruction employing a tibial transverse fixation technique according to one embodiment of the present invention.

DETAILED DESCRIPTION OF THE INVENTION

The present invention provides techniques and reconstruction systems for ligament or tendon repair that provide simpler, all-inside ACL reconstruction techniques and improved graft fixation in the tibial tunnel or socket.

According to the tibial transverse fixation techniques of the present invention, femoral and tibial sockets are provided to accommodate retrograde fixation of a graft (for example, a ligament, tendon or allograft such as semitendonosus allograft). At least one of the tibial and femoral sockets or tunnels is formed by using a retrograde cutter, for example, a retrograde drill device with a flip retrograde drill cutter described in U.S. Patent Appl. Publ. No. 2009/0275950, or a rotary drill cutter described in U.S. Patent Appl. Publ. No. 2004/0199166, the disclosures of both of which are incorporated by reference in their entirety herewith. Preferably, the tibial tunnel is formed by the retrograde drill method. The femoral tunnel or socket may be formed by the retrograde drill method or by a conventional method, and may be carried out before or after the formation of the tibial tunnel.

An exemplary method of ACL reconstruction employing one technique of the present invention is detailed below with reference to FIGS. 1-31. Another exemplary method of ACL reconstruction employing another technique of the present invention is detailed below with reference to FIGS. 32-38. FIGS. 39-46 illustrate schematic views of a hook and guide system (used in the tibia and femur) and of its components, employed in the method of FIGS. 32-38. Yet another exemplary method of ACL reconstruction employing another technique of the present invention (with a drill assembly different from that of FIGS. 39-46) is detailed below with reference to FIGS. 32-39.

Transverse Tibial Fixation Technique (Using a Tibial Socket and FlipCutter)

Figure 1:
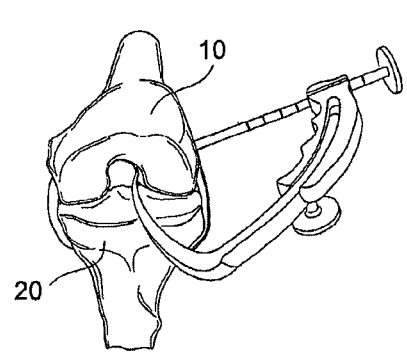
Figure 2:
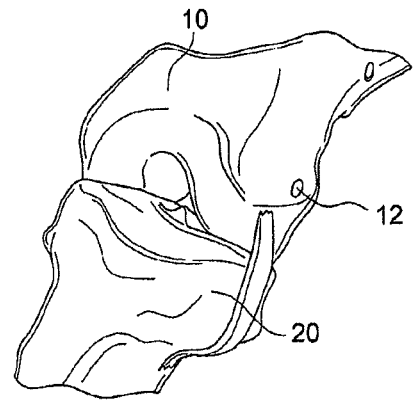

FIGS. 1 and 2: The femur 10 if prepared by drilling a full femoral tunnel 12 either by a retrograde method with a retro-drill cutter (for example, a flip retrograde drill cutter 25) or by an antegrade method with a standard reamer. Tunnel 12 can also be drilled through the medial portal with a standard reamer. FIGS. 1 and 2 show the retrograde method of forming the femoral tunnel 12. If an "all inside" option is desired, a femoral socket can be drilled.

Femoral tunnel 12 may be formed with a retrograde cutter, for example, a retrograde drill device with a flip retrograde drill cutter 25 described in U.S. Patent Appl. Publ. No. 2009/0275950, or a rotary drill cutter described in U.S. Patent Appl. Publ. No. 2004/0199166, the disclosures of both of which are incorporated by reference in their entirety herewith. As described in U.S. Patent Appl. Publ. No. 2004/0199166, the rotary drill cutter is a dual-sided rotary drill cutter that comprises two opposed sides and is provided with cutting surfaces on both sides, such that the rotary drill cutter is configured for cutting in two directions.

As described in the U.S. Patent Appl. Publ. No. 2009/0275950, flip retrograde drill cutter 25 is provided with a blade, preferably a flip blade, that is configured to articulate between at least a first "straight" position, for example, substantially parallel to a longitudinal axis of the flip retrograde cutter, and at least a second "flip" position, for example, a non-parallel position relative to the longitudinal axis of the flip retrograde cutter. The flip retrograde cutter 25 creates a recipient site socket from the inside out, i.e., using a retrograde technique, with minimal incisions of distal cortices and reduced intraarticular bone fragmentation of tunnel rims. The recipient femoral socket may be also formed in a retrograde manner (to allow retrograde fixation of a graft within two sockets, for example), by inserting the flip retrograde cutter 25 in the "straight" configuration into the joint space, preferably from the outside in, through a small diameter tunnel. A locking tube of the instrument is then retracted so that the blade can be articulated into the "flip" configuration, i.e., into a position other than the "straight" position and preferably at about 90 degrees to the longitudinal axis of the instrument. The device 25 is locked in the "flip" position by tightening the locking tube. A socket is created by conducting a drilling operation, i.e., by rotating the instrument, while the device is pulled outwardly (i.e., from the inside of the articular joint to the outer cortex of the bone). The blade of the device 25 is configured to drill in an antegrade manner when in the "straight" position and to cut in a retrograde manner when in the "flip" position.

Figure 3:
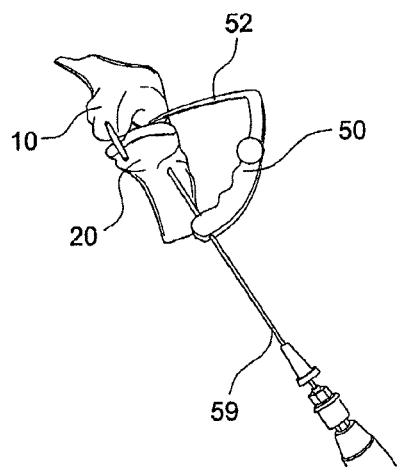
Figure 4:
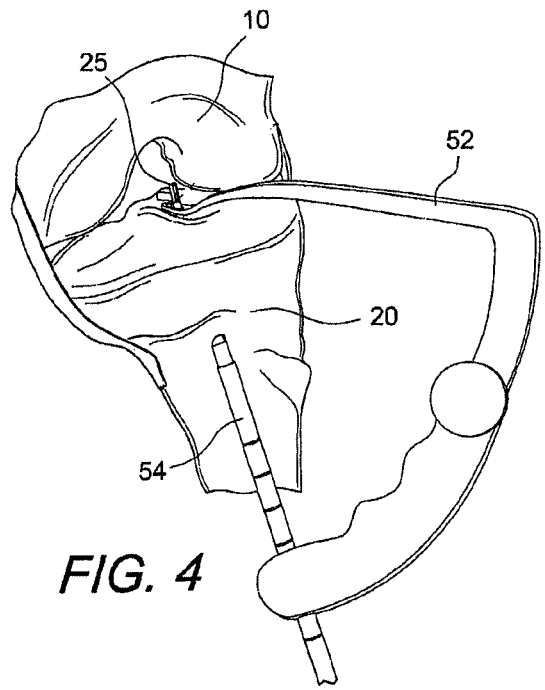

FIGS. 3 and 4: A hook and guide system 50 (RetroConstruction guide 50) including marking hook 52, handle 51 having a C-ring configuration and drill sleeve 54 is used to place FlipCutter Pin 59 into tibia 20 (to further accommodate flip retrograde drill cutter 25 into tibia 20).

Figure 5:
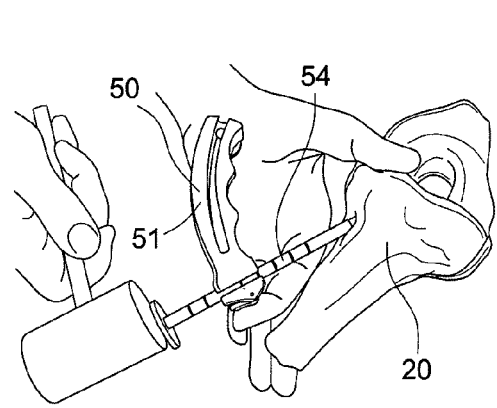
Figure 6:
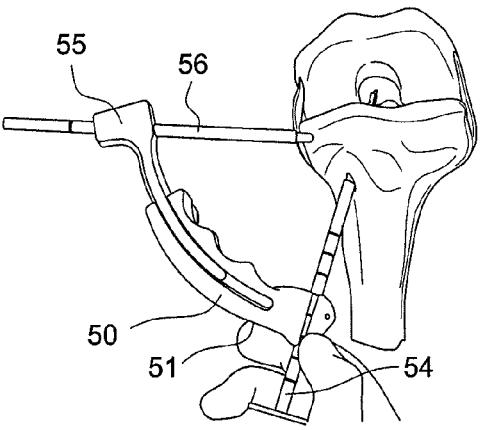

FIGS. 5 and 6: Tibial ACL marking hook 52 is removed, and the tip of drill sleeve 54 is tapped into bone 20. Guide 55 (Transfix guide 55) is placed into handle 51 of hook and guide system 50 (RetroConstruction guide 50). Drill sleeve 56 is placed in guide 55 (FIG. 6). For pediatric patients, the angle and alignment of guide may be adjusted so that the drill pin 58 (FIG. 7) will cross above growth plate (may use X-ray). Pin can be placed medial to lateral or lateral to medial.

Figures 7, 8:
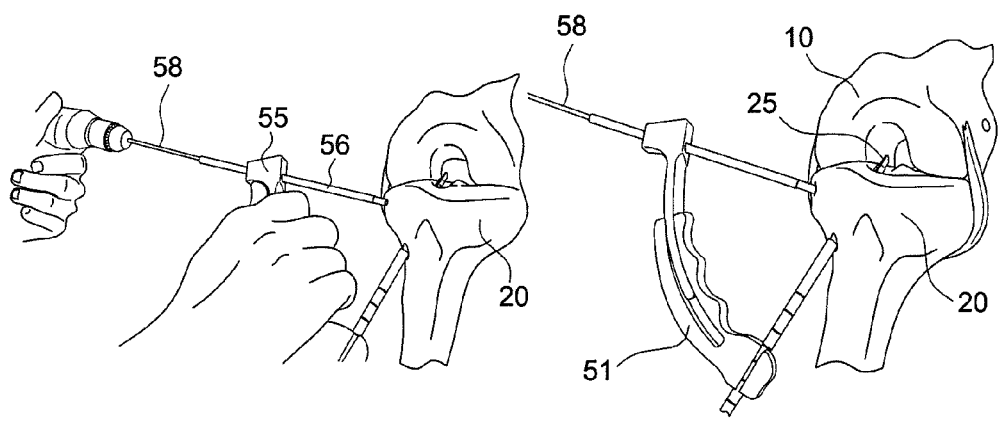

FIGS. 7 and 8: Pin 58 (transverse pin or transfix pin 58) is drilled through sleeve 56 into tibia 20 until it gets close to or hits FlipCutter Pin 59 in bone. Pin 58 is backed up to make room for flip retrograde drill cutter 25 to prepare the tibial socket.

FIGS. 9 and 10: Flip retrograde drill cutter 25 is used to prepare a tibial socket 66 to desired depth. In pediatric patients, drilling is done above growth plate.

FIGS. 11 and 12: Leaving flip retrograde drill cutter 25 in place at bottom of socket, the transverse drill pin 58 is drilled across tibia 20. Tibial socket 66 (FIG. 12) is visualized to ensure the drill pin 58 crosses the socket 66 appropriately.

Figure 13:
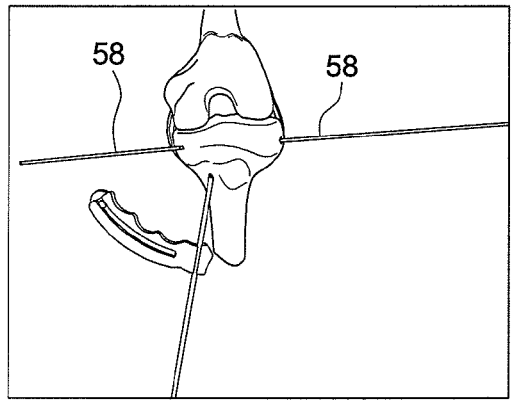
Figure 14:
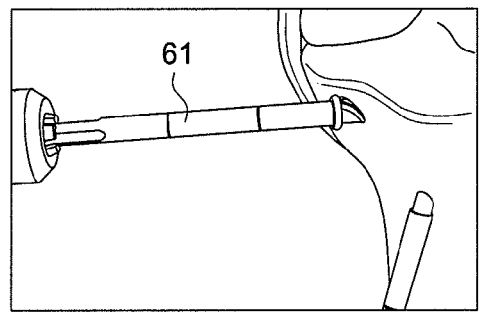

FIGS. 13 and 14: Once transverse drill pin 58 is in place, the cortex is over reamed with drill 61 to make room for the head of the implant 88.

Figure 15:
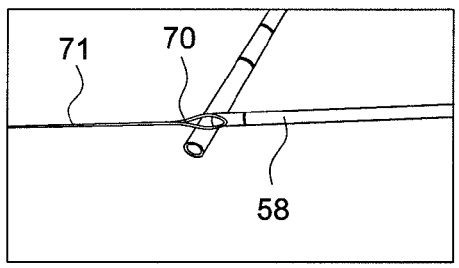
Figure 16:
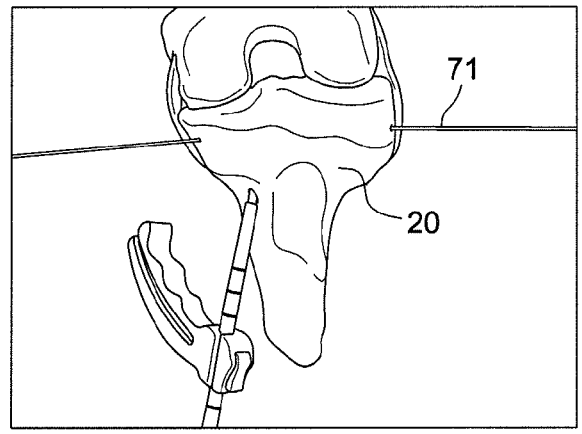

FIGS. 15 and 16: Loop 70 from the nitinol graft passing wire 71 is placed into the slot in the transverse pin 58. Pin 58 is pulled out of the bone 20, which pulls the wire 71 across the tibia 20 (FIG. 16).

Figure 17:
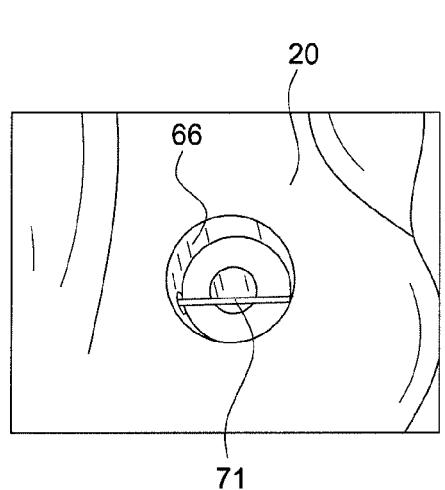
Figure 18:
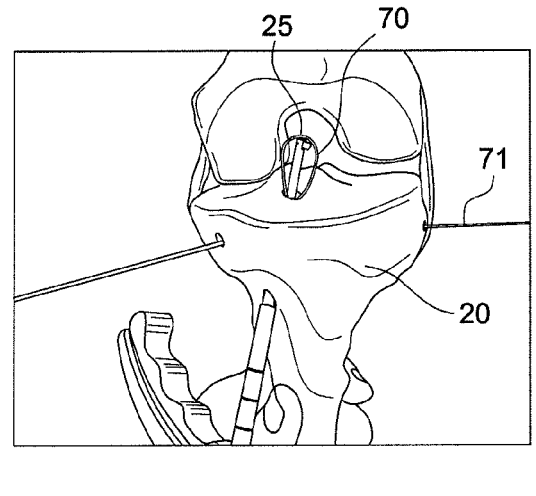
Figure 19:
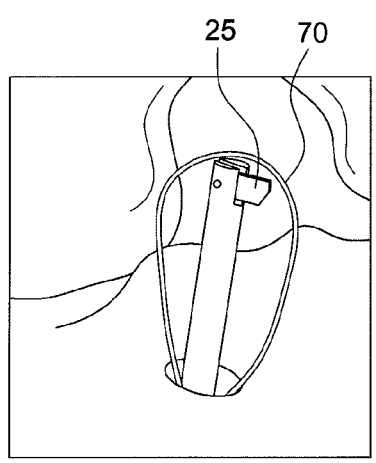

FIGS. 17, 18 and 19: The flip retrograde drill cutter 25 is used to push the nitinol graft passing wire 71 into the joint space. Flip retrograde drill cutter 25 is now be removed from the knee.

Figure 20:
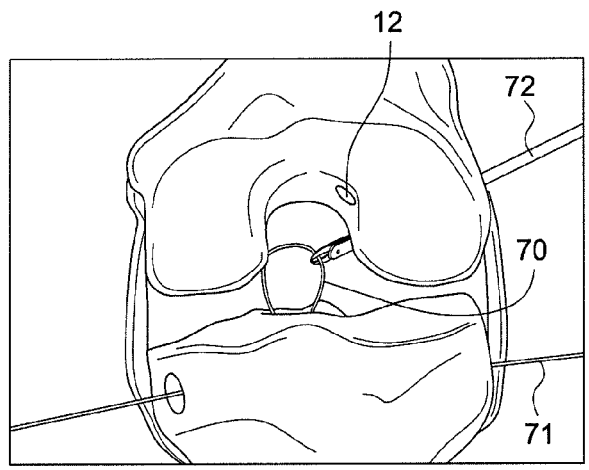

FIG. 20: For full femoral tunnels, wire 71 is pulled out of the femoral tunnel 12 with a grasper 72 (FIG. 20). For all-inside techniques, the wire is pulled out the medial portal.

Figure 21:
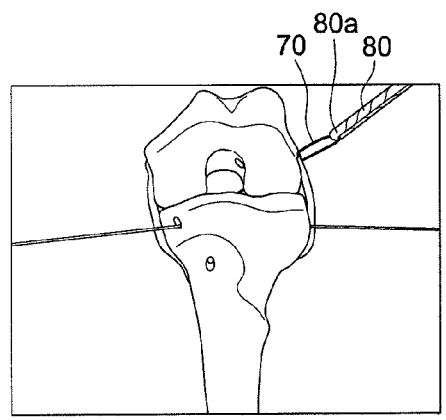
Figure 22:
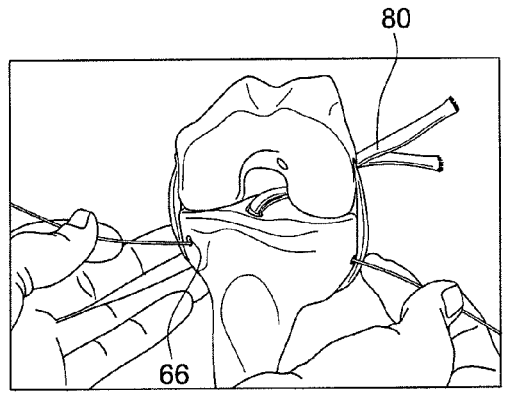

FIGS. 21 and 22: Graft 80 is placed into the nitinol wire loop 70 so that loop 80a of folded graft 80 engages loop 70 of wire 71. The ends of the nitinol wire 71 are pulled to advance graft 80 into the tibial socket 66.

Figure 23:
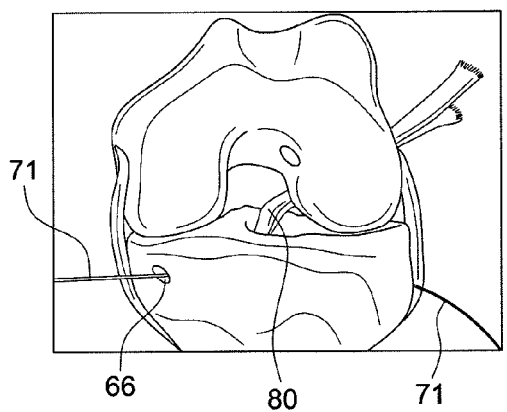
Figure 24:
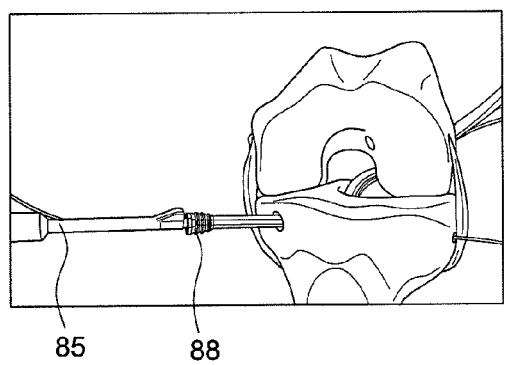

FIGS. 23 and 24: Transverse implant 88 is placed over wire 71 and the implant 88 is malleted into place. The implant 88 is inserted over the guide wire 71 and advanced until its conical end 89 contacts the tibia. An implant impactor is chucked into driver/extractor 85 and placed over the wire 71. The head of the implant 88 is engaged and a mallet may be used to drive the implant into the tibia until a depth stop on the driver contacts the cortical bone. Pulling on tendon 80 is avoided during impaction of the transverse implant 88.

Figure 25:
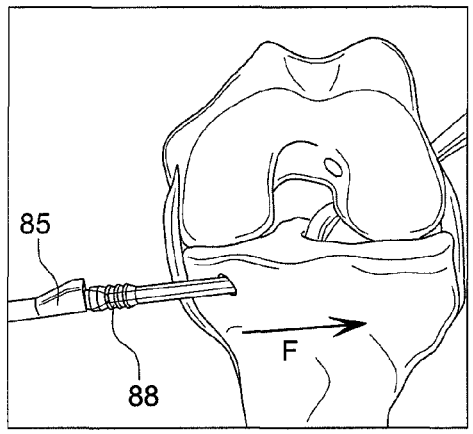
Figure 26:
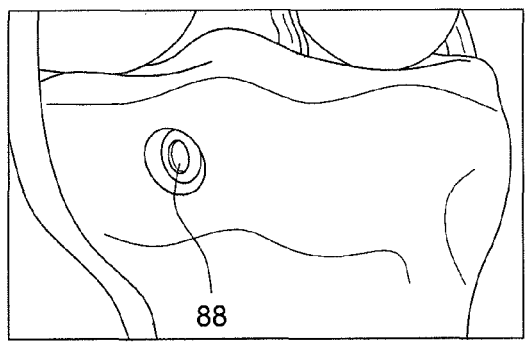

FIGS. 25 and 26: Transverse implant 88 is advanced until it is flush with tibia 20. The implant 88 is advanced along the wire 71 in the direction of arrow F (FIG. 25). The implant 88 passes over loop 80a formed in tendon 80, to provide cross-pin support of tendon 80. If removal of the implant should become necessary, reverse cutting threads (which may be provided in the implant) facilitate removal by unscrewing the implant with a screwdriver, for example.

Transverse implant 88 is provided with a conical portion 89 (shown more clearly in FIG. 42) at its most distal end 88b and a threaded area with helical threads 90 (or conical ribs) at its most proximal end 88a. The implant is also cannulated to allow it to be received over wire 71 (as detailed above). The implant is further provided with a drive socket to allow the implant to be driven by impaction into the bone and then, if necessary, to be subsequently removed by screw rotation.

Figure 27:
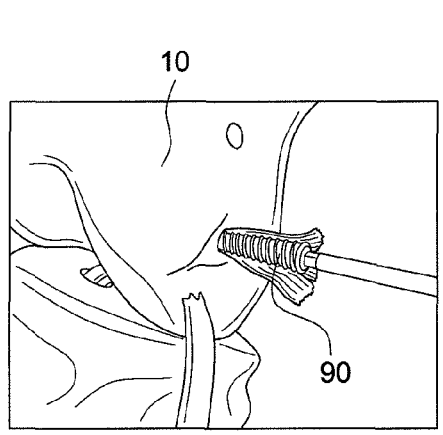
Figure 28:
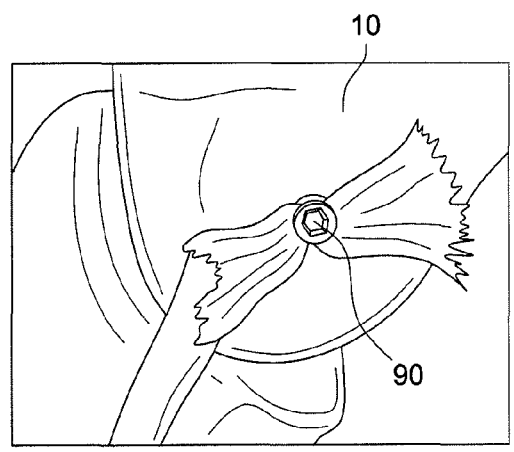

FIGS. 27 and 28: The femoral side of the graft 80 is tensioned and fixed. In the illustrated exemplary embodiment, a fixation device such as, for example, an interference screw 90 is used from outside in. Fixation of the graft within a femoral socket may be also achieved by employing a continuous loop/button construct, as described in U.S. Patent Appl. Publ. No. 2008/0046009, the disclosure of which is herein incorporated by reference. The button has an oblong configuration and a width that is preferably less than about 1 mm narrower than the width of the femoral hole through which the button is inserted and subsequently passed through. A continuous loop for supporting the graft 80 passes through eyelets in the button. The button rests on the femoral cortex.

Figures 29, 30, 31:
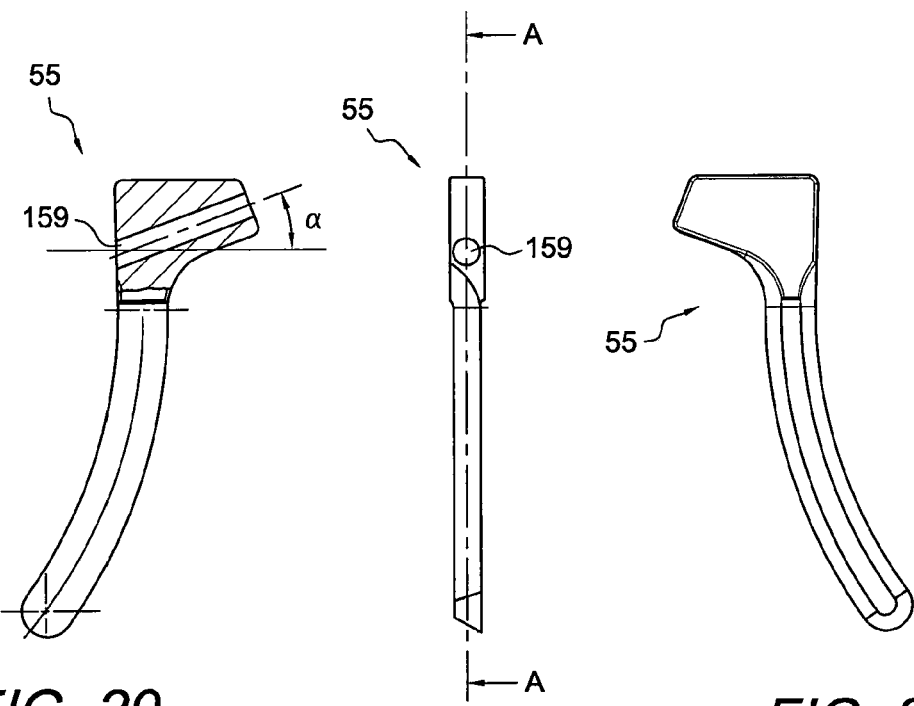
FIGS. 29-31 illustrate a cross-sectional view, a left side lateral view, and a top view, respectively, of a fixation guide used for fixating a graft according to the technique of the present invention.

FIGS. 29-31 illustrate details of tibial guide 55 used with the handle of hook and guide system 50 (shown in FIGS. 6-11) and employed for fixating a graft according to an "all-inside" tibial fixation technique of the present invention. Guide 55 includes a passageway 159 at an angle α oriented to allow for drilling parallel to the tibial plateau above the growth plate for optimal graft placement.

Transverse Fixation All-Inside Fixation Technique (with Top-Hat or Guide Piece)

FIGS. 32-38 illustrate various steps of a method of ACL reconstruction employing a tibial "all-inside" fixation technique according to another embodiment of the present invention. This approach is different from the previous embodiment which was more of a medial-lateral approach, while this embodiment uses a more anterior-posterior approach. This approach also employs a tibial guide 155 with a tibial hook 152 and a guide piece 160 (a guide member 160 in the form of a "top-hat" 160) that ensures transverse drilling and correct positioning of a transfix implant for cross-pin fixation of a graft (for example, an Anterior. Tibialis allograft) in the tibial tunnel (on the tibial side, close to the jointline, by a single incision and with cortical fixation). The proximal end of the guide piece is designed to engage additional components of guide system 150 such as extension sleeves or drills (such as step drills) or impactors, for example, and as detailed below.

Figure 32:
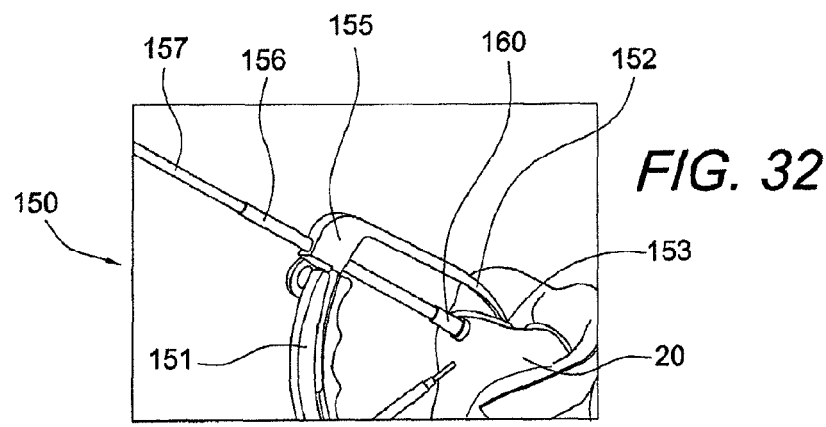
FIGS. 32-38 illustrate various steps of a method of ACL reconstruction employing a tibial transverse fixation technique according to another embodiment of the present invention.

FIG. 32: Hook and guide system 150 comprising handle 151 (hand grip 151) having a C-ring configuration, tibial hook 152 (with tibial hook eye 153) and "top-hat" 160 (guide member or guide piece 160) at one end of the handle 151, and guide sleeve 156 at the other end of handle 151 is assembled, and then positioned on tibia 20. The flip cutter 25 is drilled until it emerges through the tibial hook eye 153. The step drill 157 is drilled through extension sleeve 156 until the flip cutter is reached. It is important to ensure that the assembly 150 is stable on the tibia 20 before impacting the top-hat 160 with a slide hammer, for example.

Top-hat 160 (guide piece 160) is provided with a central body 161 (FIG. 33) having a cylindrical configuration and a plurality of spikes or protuberances (not shown) provided at the most distal end of the central body, to ensure adherence to the tibial cortex. When guide piece 160 is secured to the bone (tibia), annular lip 167 at the distal end of the guide piece engages the bone cortex and further stabilizes the guide piece.

Figure 33:
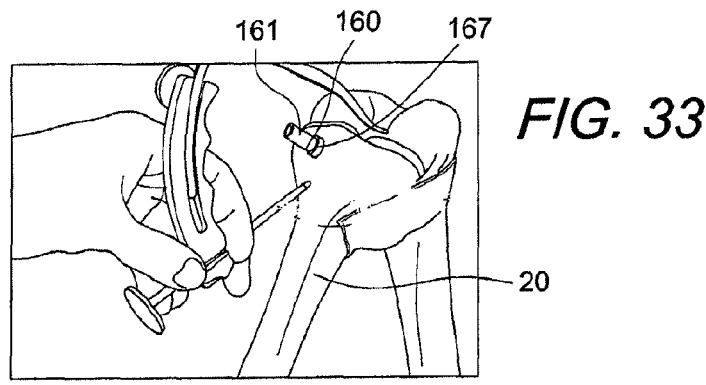

FIG. 33: The extension sleeve 156 is removed from the top-hat 160.

Figure 34:
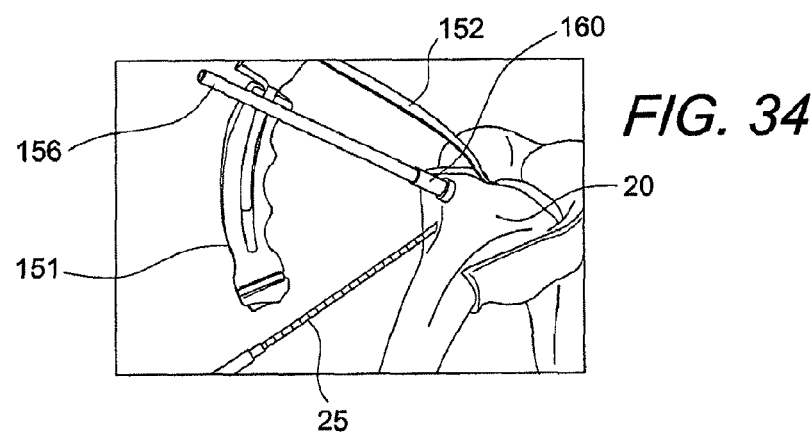

FIG. 34: The handle 151, the tibial hook 152 and the step drill 157 are disassembled and removed.

Figure 35:
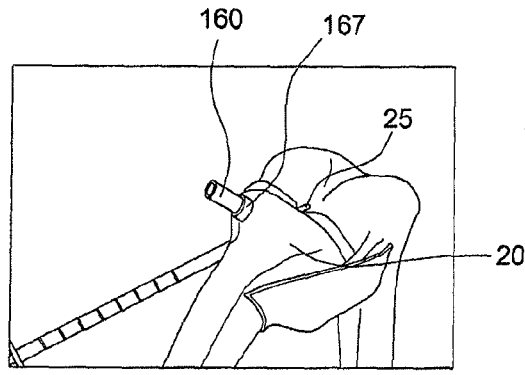

FIG. 35: The flip retrograde drill cutter 25 is drilled in a retrograde manner to create the tibial socket 66 (retrodrill the flipcutter slot).

Figure 36:
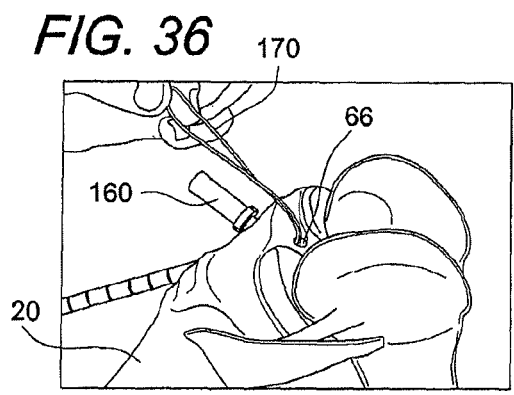
Figure 37:
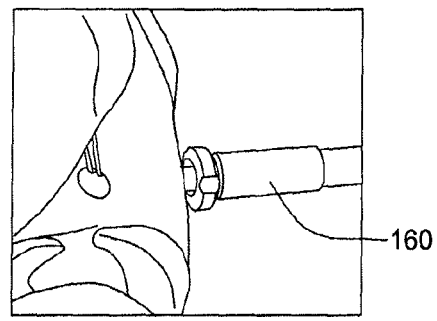

FIGS. 36 and 37: At this stage, the method steps are similar to those illustrated above with reference to FIGS. 15-28. The suture shuttle 170 is advanced up into joint space. Optionally, alignment is checked—the drill is re-inserted and position in the middle of graft tunnel is checked. Optionally, full depth drilling is performed—drill stepped drill to cortical shoulder stop (avoid suture).

Figure 38:
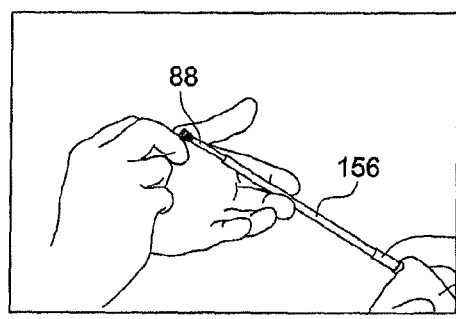
Figure 39:
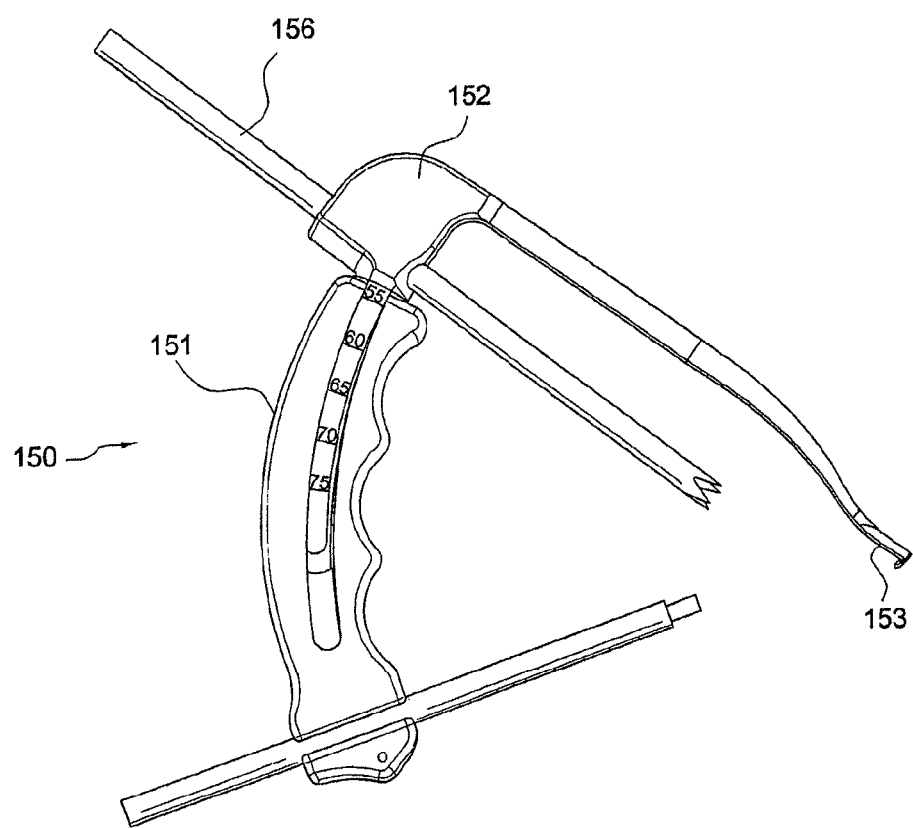
FIG. 39 illustrates a schematic view of a hook and guide system (used in the tibia and femur) employed in the method of FIGS. 32-38.
Figure 40:
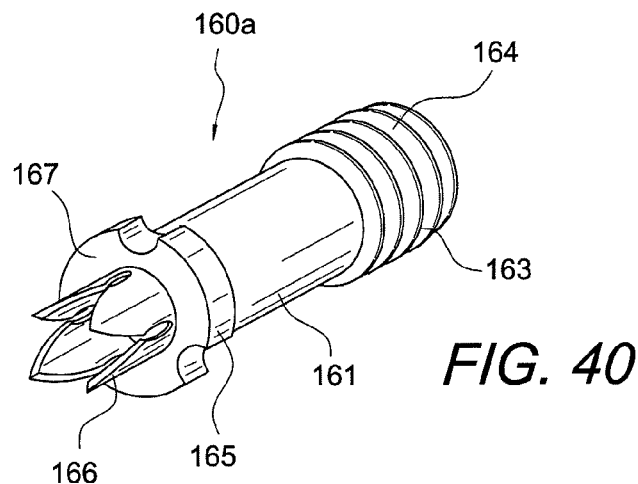
FIGS. 40-46 illustrate various views of components of the hook and guide system employed in the method of FIGS. 32-38.

FIG. 38: Graft 80 is advanced into position with suture 170. The implant 88 is inserted into top-hat 160 (using the extension sleeve if necessary). Implant 88 is impacted into final position. With impactor 190 in position to "lock" the assembly together, the top-hat 160 is removed. The implant 88 pierces the tails of the graft to secure the graft in socket.

Figure 42:
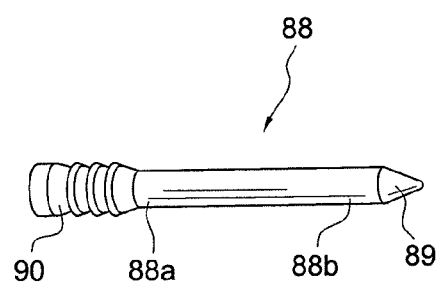

Implant 88 may have the configuration shown in FIG. 42, or may have different configurations, for example with respect to the threaded area 90 and/or other design characteristics of the implant.

The technique described above with reference to the formation of tibial socket 66 may be employed, in the same manner, for the formation of the femoral socket 12. Subsequent to the tibial fixation, the femoral fixation of the graft may proceed as known in the art, for example, by employing a fixation device such as an interference screw or a continuous loop/button construct, as described in U.S. Patent Appl. Publ. No. 2008/0046009, the disclosure of which is herein incorporated by reference. The button has an oblong configuration and a width that is preferably less than about 1 mm narrower than the width of the femoral hole through which the button is inserted and subsequently passed through. A continuous loop for supporting the graft 80 passes through eyelets in the button. The button rests on the femoral cortex.

As described above, the femoral and tibial sockets may be prepared by employing a retrogade cutter, for example, a retrograde flip cutter device in the manner described in U.S. Patent Appl. Publ. No. 2009/0275950.

The use of the flip retrograde drill cutter and the stepped drill sleeve makes it very easy and reliable for the surgeons to keep the tibial cortex intact. The fixation technique provides the surgeons with:

1. improved aperture/cortical tibial fixation which minimizes tibial tunnel widening that causes problems in many ACL revision cases involving retrograde screw insertion;
2. a fast and easy way for conducting an all-inside procedure for surgeons who have difficulty using a retrograde screw; and
3. reduced graft displacement.

The invention also provides at least two different tibial hooks with 20°/25° angle option, as well as with a 15°/10° option or alternatively an adjustable angle (the surgeon drills the tibial drill pin and places the tibial hook on the tibia plateau). It is important for the surgeon to maintain the system parallel to the tibial plateau to avoid the risk of placing the pin into the plateau and to countersunk the pin into the anterior tibial cortex. The hook of the present invention provides "flexible hook adjustment" with only one hook instead of 3-4 different angle types.

The embodiment described above employs a guide piece or guide member 160 (top-hat 160) that was illustrated as having a specific configuration (i.e., a cylindrical configuration as shown in FIG. 33, for example). The guide piece 160 is not limited to this configuration, however, and the invention contemplates embodiments wherein the guide piece has any other configuration, for example, the conical configuration 160b shown in FIGS. 50-53 or the configuration 160a shown in FIGS. 40-46.

Figure 41:
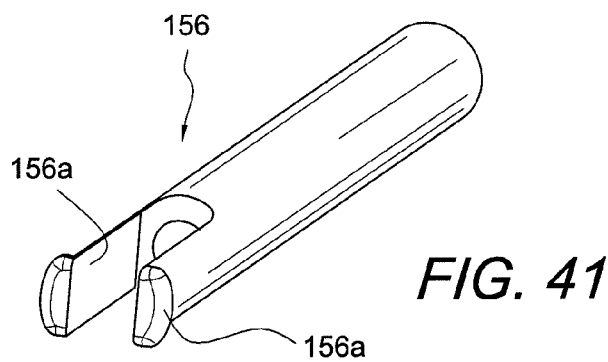

Guide piece 160a of FIGS. 40 and 43-46 is provided, for example, with a central body 161 having a cylindrical configuration with a proximal end 163 and a distal end 165 and a plurality of spikes (protuberances) 166 that ensure adherence to the tibial cortex. When guide piece 160a is secured to the bone (tibia), annular lip 167 at the distal end 165 engages the bone cortex and further stabilizes the guide piece. Proximal end 163 is provided with a plurality of ribs 164 (external and internal) that allow engagement of a plurality of arms or flanges 156a (for example, two opposing arms 156a as shown in FIG. 41) formed of resilient material and as part of extension sleeve 156 (that is designed to engage the internal ribs 164 of the guide piece 160a of FIG. 40).

Figure 43:
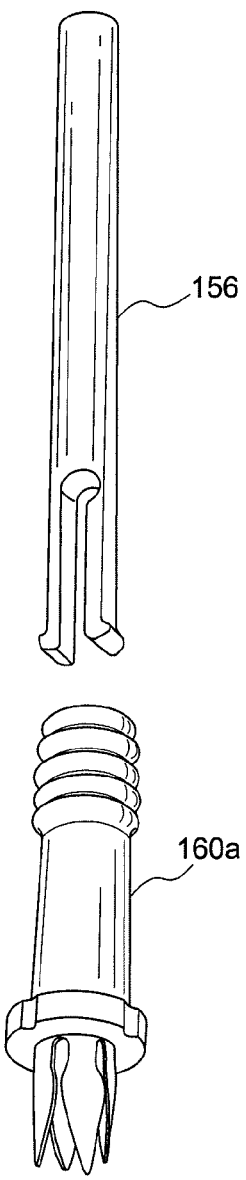
Figure 44:
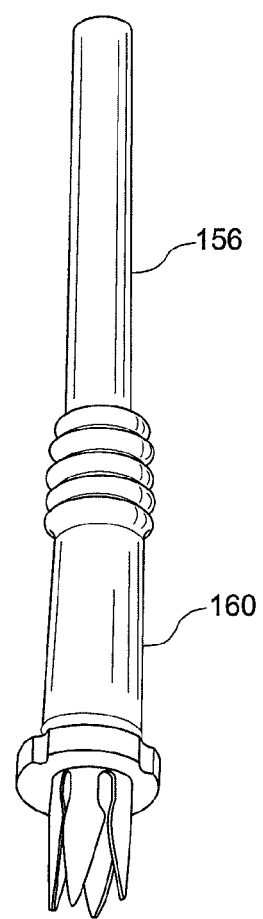
Figure 45:
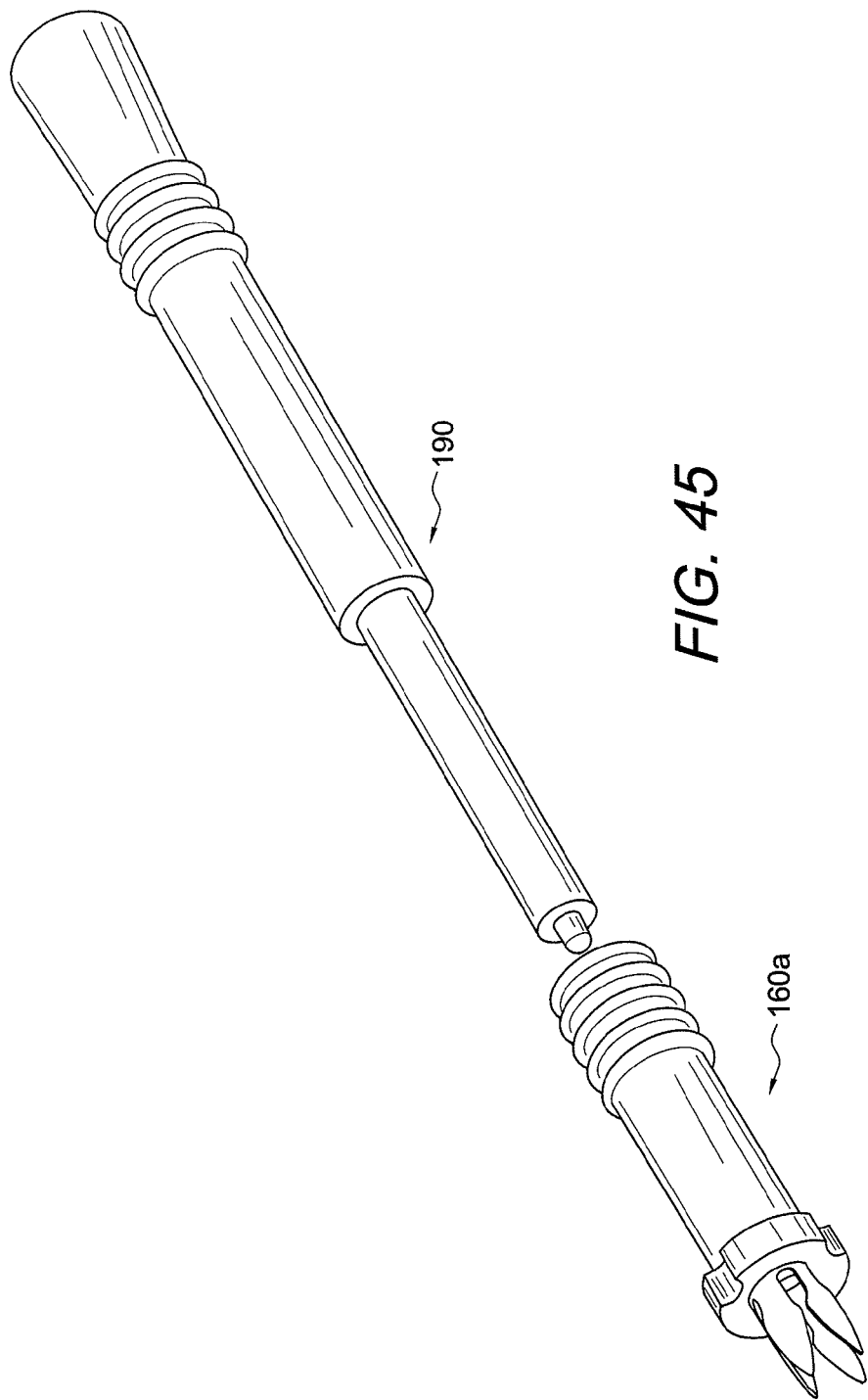
Figure 46:
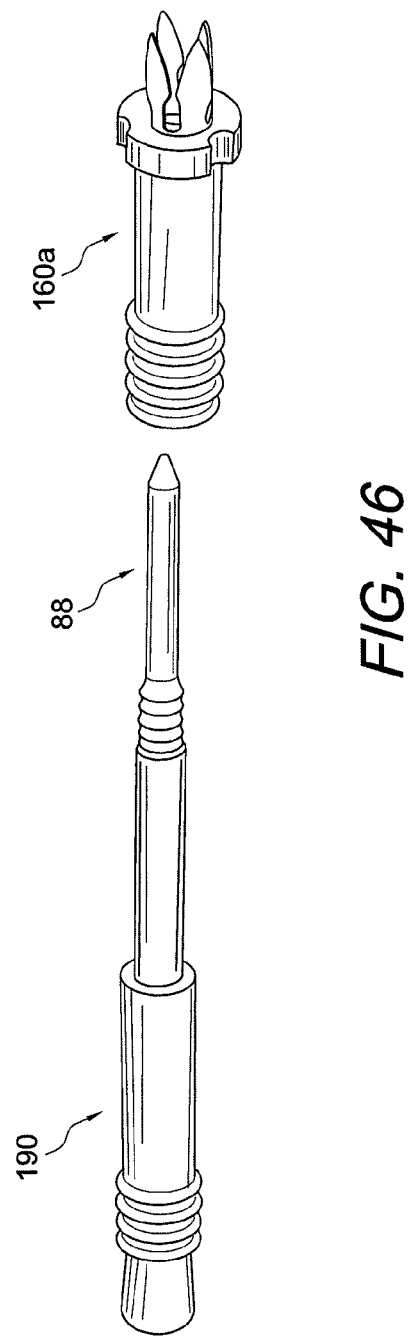

FIGS. 43 and 44 illustrate the guide piece 160a and sleeve 156 prior to engagement (FIG. 43) and after engagement (FIG. 44). FIG. 45 illustrates the guide piece 160a prior to engagement to impactor 190. FIG. 45 illustrates the guide piece 160a prior to engagement to transverse implant 88 and impactor 190.

Transverse Fixation with Drill Assembly and Top-Hat (or Guide Piece) for Femoral and Tibial Side FIGS. 47-53 illustrate another embodiment of a method of ACL reconstruction employing a transverse tibial fixation technique. This approach is similar to the previously-described embodiment (detailed in FIGS. 32-38 and with reference to the guide piece 160a of FIGS. 39-46) but differs in that both guide piece 160b (top-hat 160b) and guide piece impactor 190b have a conical configuration. The guide piece 160b (in the form of a "top-hat") ensures transverse drilling and correct positioning of a transfix implant for cross-pin fixation of a graft (for example, an Anterior Tibialis allograft) in the tibial tunnel (on the tibial side, close to the jointline, by a single incision and with cortical fixation). The proximal end of the guide piece is designed to engage additional components such as extension sleeves or drills (such as step drills) or impactors, among others.

As in the previously-described embodiment, and as shown in FIGS. 50-53, guide piece or guide member 160b is provided with a central body 161b having a generally conical configuration with a proximal end 163 and a distal end 165 and a plurality of spikes (protuberances) 166 that ensure adherence to the tibial cortex. When guide piece 160b is secured to the bone (tibia), annular lip 167 at the distal end 165 engages the bone cortex and further stabilizes the guide piece.

Figure 47:
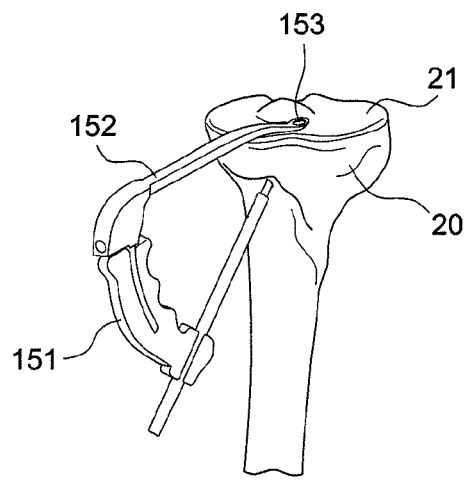
FIGS. 47-53 illustrate various steps of a method of ACL reconstruction employing a tibial transverse fixation technique according to another embodiment of the present invention.

FIG. 47 shows placement of tibial hook 152 (with tibial hook eye 153 at its most distal end) on the tibial plateau 21 of tibia 20.

Figure 48:
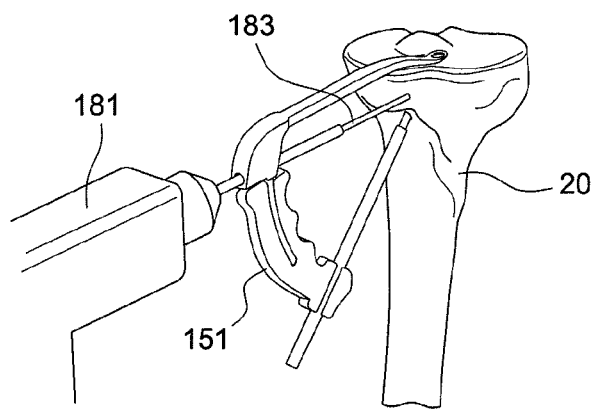

FIG. 48 illustrates drilling of the transversal drill 183 via the drill extension 181.

Figure 49:
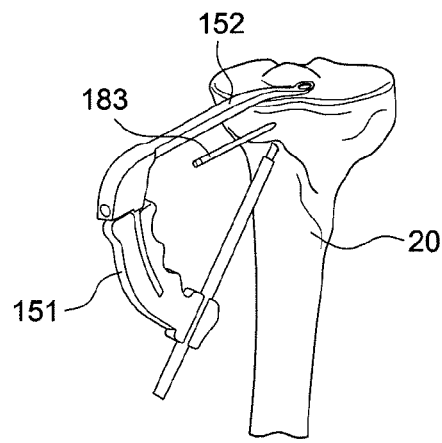

FIG. 49 shows the disconnection of the drill extension 181 from the drill with the drill 183 remaining in place to secure orientation.

Figure 50:
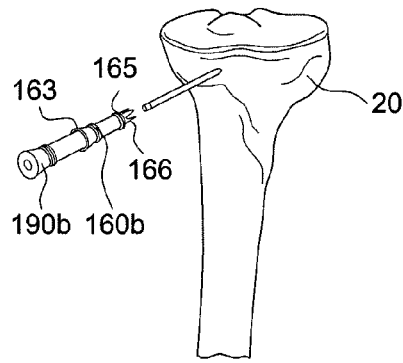

FIG. 50 shows the advancement of the guide piece (top-hat) 160b with the guide piece impactor (top-hat impactor) 190b.

Figure 51:
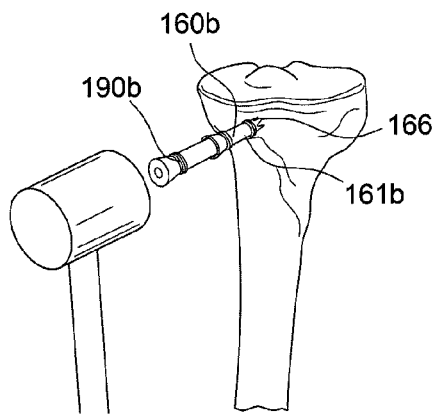

FIG. 51 illustrates the impaction of the guide piece (top-hat) 160b via guide piece impactor (top-hat impactor) 190b.

Figure 52:
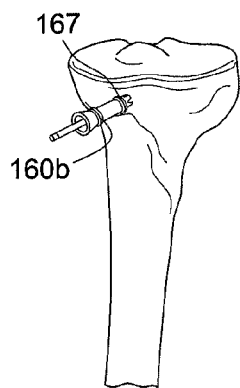

FIG. 52 shows the disassembly of the guide piece impactor (top-hat impactor) 190b from the guide piece 160b.

Figure 53:
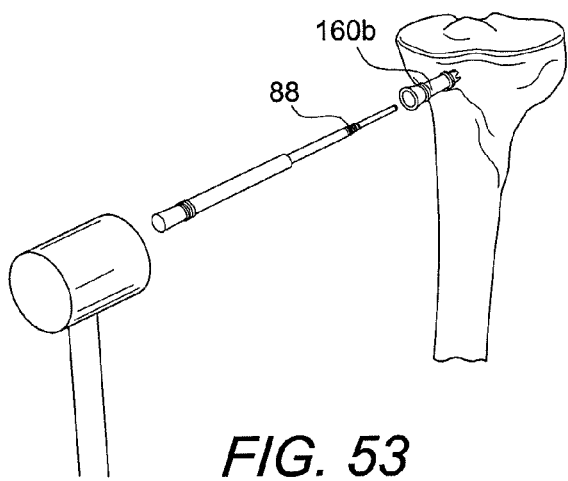

FIG. 53 shows the impaction of the transverse (T3) implant 88.

The embodiments above provide cross-pin fixation of a graft (for example, a ligament, tendon or allograft such as an anterior tibialis allograft) on the tibial side, close to the joint-line, by a single incision and with cortical fixation, while offering an easy and reliable way for the surgeons to keep the tibial cortex intact. The fixation techniques also allow surgeons to use these techniques on pediatric patients that still have active growth plates. In pediatric patients, the drilling is conducted transversely through the tibia and the tibial socket above the growth plate. In one embodiment, the graft is looped around the transverse implant, while in another embodiment, the tails of the graft are speared in the tibial socket.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed as new and desired to be protected by Letters Patent of the United States is:

1. A method of surgery, comprising the steps of:
    forming a tibial socket in tibia by drilling with a retrograde cutter from an articular surface of the tibia and into the tibia, the tibial socket having an entrance in communication with an articular joint space and a sidewall;
    introducing a flexible strand transversely into the tibial socket through the sidewall of the tibial socket;
    pushing the flexible strand with the retrograde cutter into the articular joint space and pulling a portion of the strand out through the socket entrance to form a loop in the flexible strand outside the entrance to the tibial socket;
    engaging a graft, in the articular joint space, with the loop of the flexible strand out of the socket entrance; and
    pulling the flexible strand and the graft engaged thereto into the tibial socket.

2. The method of claim 1, wherein the step of forming a tibial socket further comprises forming the socket in a retrograde manner by introducing a guide pin through the tibia, introducing the retrograde cutter into the joint space, and retrograde cutting into the tibia from the articular surface of the tibia and into the tibia.

3. The method of claim 2, wherein the retrograde cutter is a dual-sided rotary drill cutter comprising two opposed sides provided with cutting surfaces on both sides, such that the rotary drill cutter is configured for cutting in two directions.

4. The method of claim 2, wherein the retrograde cutter is a flip retrograde cutter comprising a shaft and a blade at a distal end of the shaft, the blade being securely engaged to the shaft and capable of movement from a first position generally aligned with the longitudinal axis of the body to a second position which is not aligned with the longitudinal axis.

5. The method of claim 1, further comprising the step of forming a loop in the graft and engaging the loop in the graft with the loop of the flexible strand pulled out through the tibial socket.

6. The method of claim 1, further comprising the step of supporting the graft in the tibial socket.

7. The method of claim 6, wherein the step of supporting the graft in the tibial socket is performed using a transverse implant.

8. The method of claim 7, wherein the transverse implant is cannulated, the method further comprising the step of guiding the transverse implant using the strand.

9. The method of claim 1 further comprising the step of providing a guide system comprising a handle, a hook attached to the handle, and a guide including a passageway oriented at an angle to allow drilling about parallel to the tibial plateau.

10. The method of claim 1 further comprising the step of drilling transversely through the tibia and the tibial socket, and above the growth plate in a pediatric patient.

11. The method of claim 1 further comprising the steps of attaching the graft to a fixation device and subsequently securing the graft in the femur.

12. The method of claim 11, wherein the fixation device is a suture/button loop construct having a button with at least one eyelet and a continuous suture loop attached to the eyelet.

13. The method of claim 12 further comprising the steps of positioning the graft attached to the suture/button loop construct into a femoral socket, and securing the button to the femoral cortex.

14. The method of claim 13, wherein the femoral socket is formed by retrograde drilling from an articular surface of the femur and into the femur, by accessing the articular surface of the femur and drilling so that an opening of the femoral socket is flush with the articular surface of the femur and another opening of the femoral socket is located within the femur.

15. A method of cross-pin ACL reconstruction, comprising the steps of:
    forming a tibial socket in tibia in a retrograde manner by drilling with a retrograde cutter from an articular surface of the tibia and into the tibia, the socket having an entrance in communication with an articular joint space and a sidewall;
    drilling a guide pin through a guide member oriented about parallel to the tibial plateau, and through the sidewall of the bone tibial socket so as to transversely intersect the tibial socket;
    pulling a flexible strand transversely through the guide member and through the tibial socket using the guide pin;
    pushing the flexible strand with the retrograde cutter into the articular joint space to form a loop in the flexible strand and pulling the loop in the flexible strand out through the entrance of the tibial socket;
    engaging a graft, in the articular joint space, with the loop in the flexible strand pulled out of the entrance of the tibial socket;
    pulling the flexible strand in a direction transverse to the tibial socket so as to draw the graft engaged therewith into the tibial socket;
    passing an implant transversely through a loop formed in the graft in the tibial socket; and
    securing the graft in a femoral socket by attaching the graft to a fixation device.

16. The method of claim 15 further comprising the step of drilling transversely through the tibia and the tibial socket above the growth plate.

17. The method of claim 15, wherein the guide member is provided with spikes for engaging the tibial cortex.

18. The method of claim 15, wherein the femoral socket is formed in a retrograde manner.

19. The method of claim 15, wherein the graft is a ligament, a tendon, or an allograft.

20. The method of claim 15, wherein the fixation device is an interference screw or a suture/button loop construct having a button with at least one eyelet and a continuous suture loop attached to the eyelet.

* * * * *